United States Patent
Boutinon et al.

(10) Patent No.: US 12,245,809 B2
(45) Date of Patent: Mar. 11, 2025

(54) OPTOMETRY DEVICE FOR TESTING AN INDIVIDUAL'S EYE AND ASSOCIATED METHOD

(71) Applicant: Essilor International, Charenton-le-Pont (FR)

(72) Inventors: Stéphane Boutinon, Charenton-le-Pont (FR); Léonard Hartmann, Charenton-le-Pont (FR); Bernard Brechemier, Charenton-le-Pont (FR); Mai-Lan Boytard, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 635 days.

(21) Appl. No.: 17/440,044

(22) PCT Filed: Mar. 20, 2020

(86) PCT No.: PCT/EP2020/057863
§ 371 (c)(1),
(2) Date: Sep. 16, 2021

(87) PCT Pub. No.: WO2020/188104
PCT Pub. Date: Sep. 24, 2020

(65) Prior Publication Data
US 2022/0142470 A1    May 12, 2022

(30) Foreign Application Priority Data
Mar. 20, 2019   (EP) .................................... 19305342

(51) Int. Cl.
*A61B 3/032*    (2006.01)
*A61B 3/00*     (2006.01)

(52) U.S. Cl.
CPC ............ *A61B 3/032* (2013.01); *A61B 3/0041* (2013.01)

(58) Field of Classification Search
CPC ........ A61B 3/032; A61B 3/0041; A61B 3/103
(Continued)

(56) References Cited

U.S. PATENT DOCUMENTS 3,969,020 A   7/1976  Lynn et al.
4,298,253 A   11/1981 Tagnon
(Continued)

FOREIGN PATENT DOCUMENTS

CN    104159498 A    11/2014
EP    3 298 952 A1    3/2018
(Continued)

OTHER PUBLICATIONS

Japanese Office Action issued Jan. 9, 2024 in Japanese Application No. 2021-556578 with English translation, therein, 9 pgs.
(Continued)

*Primary Examiner* — Mohammed A Hasan
(74) *Attorney, Agent, or Firm* — Oblon, McClelland, Maier & Neustadt, L.L.P.

(57) ABSTRACT

An optometry device for testing an individual's eye, includes a refraction test unit having an optical system for providing different vision correction powers close to the eye of the individual, and a display unit adapted to produce a visual test image for the individual's eye, the visual test image being visible through an exit aperture of the test unit of the optometry device. The display unit includes a screen adapted to display a test picture used in producing the visual test image and at least one optical element having an optical power. The optical element presents an active state in which it exhibits a non zero refraction power placed on an optical path of the light emitted by the screen and exiting the device (Continued)

through the exit aperture, and an inactive state in which it introduces no refractive power on the optical path.

20 Claims, 5 Drawing Sheets

(58) Field of Classification Search
USPC .......................................................... 351/239
See application file for complete search history.

(56) References Cited

U.S. PATENT DOCUMENTS

| | | | |
|---|---|---|---|
| 5,231,430 | A | 7/1993 | Kohayakawa et al. |
| 2006/0007397 | A1 | 1/2006 | Lai |
| 2006/0050238 | A1* | 3/2006 | Nakamura ............ A61B 3/0041 351/205 |
| 2009/0066915 | A1 | 3/2009 | Lai |
| 2009/0073386 | A1 | 3/2009 | Petito et al. |
| 2010/0182566 | A1* | 7/2010 | Becker ................. A61B 3/0025 351/200 |
| 2011/0013140 | A1 | 1/2011 | Lai |
| 2013/0176537 | A1 | 7/2013 | Thompson et al. |
| 2015/0342454 | A1* | 12/2015 | Foster ................... A61B 3/032 351/246 |
| 2015/0342459 | A1* | 12/2015 | Robert .................... A61B 3/04 351/200 |
| 2018/0078135 | A1* | 3/2018 | Takii .................... A61B 3/0091 |

FOREIGN PATENT DOCUMENTS

| | | |
|---|---|---|
| EP | 3 381 350 A1 | 10/2018 |
| JP | 59-85640 A | 5/1984 |
| JP | 5 126 A | 1/1993 |
| JP | H07-299032 | 11/1995 |
| JP | H07-327928 | 12/1995 |
| JP | 2018-171228 A | 11/2018 |
| WO | WO 2015/107303 A1 | 7/2015 |
| WO | WO 2015/155458 A1 | 10/2015 |
| WO | WO 2018/054997 A1 | 3/2018 |

OTHER PUBLICATIONS

Combined Chinese Office Action and Search Report issued Nov. 28, 2023 in Chinese Patent Application No. 202080021989.8, 9 pages.
International Search Report and Written Opinion issued on May 14, 2020 in PCT/EP2020/057863 filed on Mar. 20, 2020.
Combined Chinese Office Action and Search Report issued Jul. 12, 2024, in corresponding Chinese Patent Application No. 202080021989.8 (with English Translation), 6 pages.
Office Action issued Oct. 28, 2024, in corresponding Japanese Patent Application No. 2021-556578 with English translation, citing documents 15 and 16 therein, 15 pages.

* cited by examiner

OPTOMETRY DEVICE FOR TESTING AN INDIVIDUAL'S EYE AND ASSOCIATED METHOD

TECHNICAL FIELD OF THE INVENTION

The invention relates to an optometry device for testing an individual's eye and an associated method.

BACKGROUND INFORMATION AND PRIOR ART

Document EP3298952 describes such a device. In this device, the screen is fixed. A fixed lens is positioned on the optical path of the picture displayed by the screen. The position of the eye of the individual is in the focal plane of the lens.

The field of the visual test display produced that can be seen by the eye of the individual is then rather narrow. Alignment between the visual test display and the eye is therefore crucial.

The optical distance between the screen and the aperture exit of the device may be varied by moving mirrors closer of farther away from the screen.

This arrangement only allows varying this optical distance in a reduced range and only allows producing a visual test display of narrow angular width.

SUMMARY OF THE INVENTION

Therefore one object of the invention is to provide a device with a wider range of measurements providing a more realistic measurement of the refraction adapted to the wearer.

The above objects are achieved according to the invention by providing an optometry device for testing an individual's eye, comprising a refraction test unit having an optical system for providing different vision correction powers close to the eye of the individual, and a display unit adapted to produce a visual test image for the individual's eye, said visual test image being visible through an exit aperture of said test unit of the optometry device, this display unit comprising:

a screen adapted to display a test picture used in producing said visual test image and at least one optical element having an optical power, said optical element presenting an active state in which it exhibits a non zero refraction power placed on an optical path of the light emitted by said screen and exiting the device through said exit aperture, and an inactive state in which it introduces no refractive power on said optical path, in order for the visual test image to be produced at a variable distance from said exit aperture.

In particular, in an embodiment of the invention, said optical element is movable between an active position in which it is placed on an optical path of the light emitted by said screen and exiting the device through said exit aperture, and a retracted position in which it remains out of said optical path, in order for the visual test image to be produced at a variable distance from said exit aperture.

In this embodiment of the invention, the optical element is movable between the active position, corresponding to the active state and the retracted position, corresponding to the inactive state, by a physical displacement of the optical element.

In another embodiment of the invention, said optical element is preferably fixed, non movable. It remains placed on said optical path of the light and has a variable refractive power, adjustable between a non zero value corresponding to said active state, and a zero value, corresponding to said inactive state.

In this other embodiment, a change of power of the optical element is performed between the active state in which an optical power different than zero is provided by the optical element placed on the optical path of the light emitted by said screen and exiting the device through said exit aperture, and the inactive state, in which the optical power of the optical element is set to zero. In the inactive state, the optical element therefore acts as if it was remaining out of said optical path. However, the optical element remains placed on the optical path of the light in both the active and inactive state of this optical element.

It is therefore possible, by moving the lens between the two positions or by modifying its refractive power, to modify the distance between the visual test image produced and the exit aperture of the device, and therefore to test the vision of the individual in different visual conditions, for example in condition of far vision at infinity or in conditions of intermediate or near vision.

Moreover, the optical element may thus be physically removed from the optical path of the light by a displacement to the retracted position or optically removed from the optical path by setting its refractive power to zero, for displaying the visual test image at a near vision distance from the eye of the individual. This allows displaying the visual test image with a bigger size of image in near vision conditions. The bigger size of image makes it possible to display a text to read and to center more easily the image with the exit aperture of the device.

Thanks to the optometry device according to the invention, it is thus possible to provide a visual test image at at least two different optical distances from the exit aperture, thereby providing visual test images for testing the vision of the subject in at least two different vision conditions, while reducing the overall size of the optometry device. The different vision conditions correspond here to two different distances of observation of the visual test image.

In the embodiment where the optical element is physically removable from the optical path, the fact that the optical element is mobile in and out of the optical path allows a reduction of the overall size of the optometry device needed to provide visual test images for testing the vision of the subject in at least two different vision conditions, such as near vision and far vision conditions.

The reduced size of the optometry device makes it easier to store and use by the eye care professional.

Moreover, the field of view remains sufficiently wide in all vision conditions to enable displaying a realistic visual test image, or at least a visual test image that is more realistic than it is the case in the state of the art. By more realistic, we mean that the conditions of observation of the image, such as optical distance and field of view, are close to the conditions of observation in real life.

In the embodiment where the optical element is optically removable from the optical path, by using an optical element with variable power, the variable power of this optical element may preferably be tuned or adjusted continuously over a range of values of optical power. The subject may therefore be presented with images shown at a variable distance, the distance being continuously adjustable in a corresponding range of distances, with a seamless transition between different distances.

An additional advantage of the embodiment with an optical element with variable power is to allow using a fixed (non movable) screen positioned as close as possible to the optical element, with or without one or several reflecting surfaces for folding the optical path, so as to define the most compact optometry device possible.

According to further non limiting features of the device of the invention:

- the variable distance is comprised between a distance of far vision and a distance of near or intermediate vision;
- said optical element is an optical lens;
- said optical element is movable in rotation and/or in translation between said active position and said retracted position;
- said screen is movable in translation along a reference axis between two positions corresponding to different distances between the visual test image produced and the exit aperture;
- said screen is movable in translation along two perpendicular directions for centering said screen relative to an optical axis of the optical element;
- the optical element being an optical lens in its active position, the relative position of said screen and said optical element is adjustable for the screen to be located at a distance from said optical lens equal to a back focal length of said optical lens measured along an optical axis of said optical lens;
- said visual test image comprises either the test picture displayed by said screen without influence of the optical element, reflected or not by a reflecting surface of the device or an image of said test picture projected by said optical element, reflected or not by a reflecting surface of the device;
- the relative positions of the screen, the optical element and the exit aperture are adapted to be varied in order for said distance between the visual test image and the exit aperture to be continuously varied in one or several ranges of optical distances comprised between infinity and a near vision distance;
- at least one reflecting surface is arranged in said device in order to direct the optical path of the light emitted by said screen toward the exit aperture;
- said at least one reflecting surface is movable in translation and/or in rotation between at least two positions;
- said at least one reflecting surface is moved in translation and/or in rotation to the position wherein said at least one reflecting surface directs the light emitted by said screen toward the exit aperture when the optical element is in the inactive state, that is, when it remains out of said optical path or when its refractive power is set to zero;
- the angular size of the visual test image measured as seen from the exit aperture is comprised between 5 and 25°;
- it comprises another screen adapted to display another picture, an image of this picture being superimposed with said visual test image;
- the screen is one of the following: a LCD screen, TFT screen, LED or OLED screen, serigraphy with backlight screen, display light projection screen with micro video projectors.

More precisely, the angular size of the visual test image measured as seen from the exit aperture along a horizontal axis is preferably comprised between 5 and 15°.

The invention also proposes a method for testing an individual's eye using an optometry device for testing an individual's eye, comprising a refraction test unit having an optical system for providing different vision correction powers close to the eye of the individual, and a display unit adapted to produce a visual test image for the individual's eye, said visual test image being visible through an exit aperture of said test unit of the optometry device, this display unit comprising:

- a screen adapted to display a test picture used in producing said visual test image and
- at least one optical element having an optical power,
- said optical element presenting an active state in which it exhibits a non zero refraction power placed on an optical path of the light emitted by said screen and exiting the device through said exit aperture, and an inactive state in which it introduces no refractive power on said optical path, in order for the visual test image to be produced at a variable distance from said exit aperture;

this method comprising:

- producing said visual test image for the individual's eye based on said test picture, said visual test image being visible through said exit aperture of the optometry device through which the individual's eye may look at said visual test image,
- varying said variable distance between said visual test image and said exit aperture, by changing the state of said optical element between said active state and said inactive state,
- assessing the visual perception of said visual test image by at least one eye of the individual at different distances between said visual test image and said exit aperture.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims.

In the accompanying drawings.

In the following description, identical or corresponding elements of each embodiment will be referred to with the same sign of reference and will not be described in details each time.

The optical paths of light are represented in dashed lines, the direction of propagation being indicated by arrowheads.

Mobility of the optical component is indicated by double arrows placed beside.

The invention relates to an optometry device 100; 200; 300; 400 for testing an individual's eye. Four embodiments of the optometry device 100; 200; 300; 400 according to the invention are shown on the appended figures.

This optometry device 100; 200; 300; 400 according to the invention comprises a refraction test unit 10 having an optical system for providing different vision correction powers close to the eye of the individual, and a display unit 20 adapted to produce a visual test image for the individual's eye, said visual test image being visible through an exit aperture 10A of said test unit 10 of the optometry device 100; 200; 300; 400.

The refraction test unit 10 is here separated from the display unit 20.

The refraction test unit 10 is interposed between the display unit 20 and the individual's eye. It is movable so that its position may be adjusted in front of the eyes of the individual. The display unit 20 is generally fixed. The refraction test unit 10 is movable relative to the display unit 20 so that their relative position may be adjusted.

Said refraction test unit 10 may be of any kind known to the man skilled in the art. Such refraction test unit 10 is usually called "phoropter". It is adapted to provide a variable optical correction for the individual's eye looking therethrough.

In particular, it may comprise a classical optical system for presenting different lenses with different optical powers in front of one or each eye of the individual, or no lens or a blank lens with no optical power.

The lenses with different powers are interchanged through a manual or preferably through a motorized command (not represented). These different powers are vision correction powers for the eye of the individual placed nearby.

The refraction test unit 10 preferably comprises an optical system with one or a plurality of lenses with adjustable power, such as liquid lenses.

The refraction test unit 10 is for instance a visual compensation system as described in document WO 2015/155 458.

The refraction test unit 10 for example includes a lens having a variable spherical power.

Said variable spherical power lens has for instance a deformable surface. The shape of this surface (in particular the radius of curvature of this surface, and hence the spherical power provided by the lens) can be controlled by moving a mechanical part (such as a ring), which mechanical part may be driven by a motor of the refraction test unit 10.

The refraction test unit may also include a pair of independently rotatable lenses each having a cylindrical power.

They may each be rotated by action of other motors of the refraction test unit 10.

The motors are controlled by a control unit such that the combination of the variable spherical power lens and the two cylindrical power lenses provides a desired spherical correction and a desired cylindrical correction to the individual's eye, as explained in document WO 2015/107 303.

Figure 7:
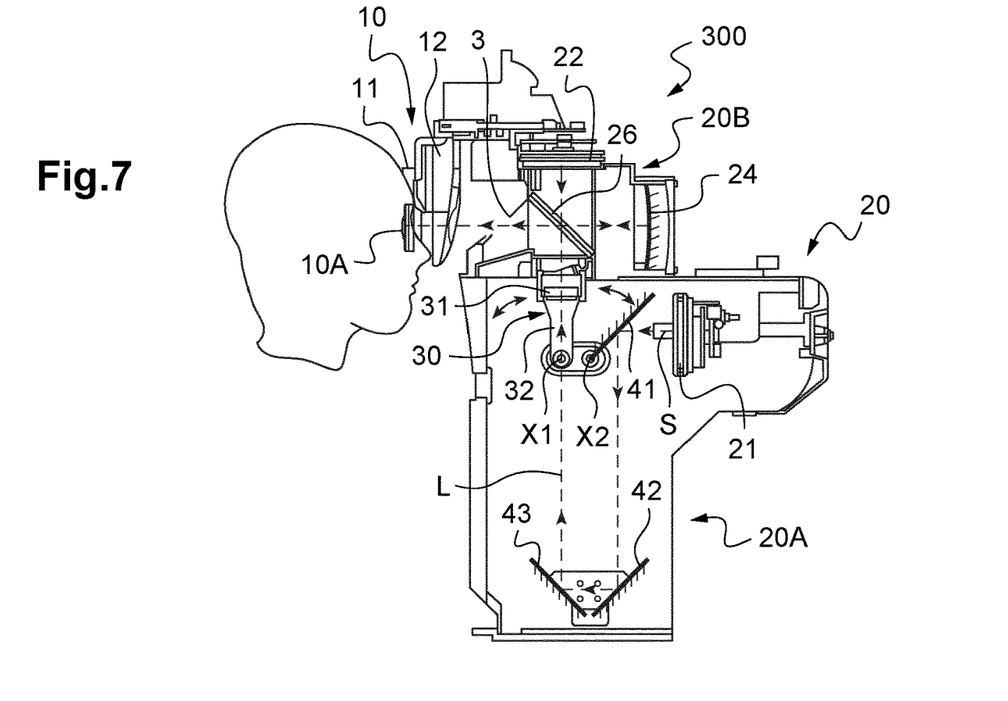
FIGS. 7 and 8 relate to a third embodiment of the invention.
Figure 8:
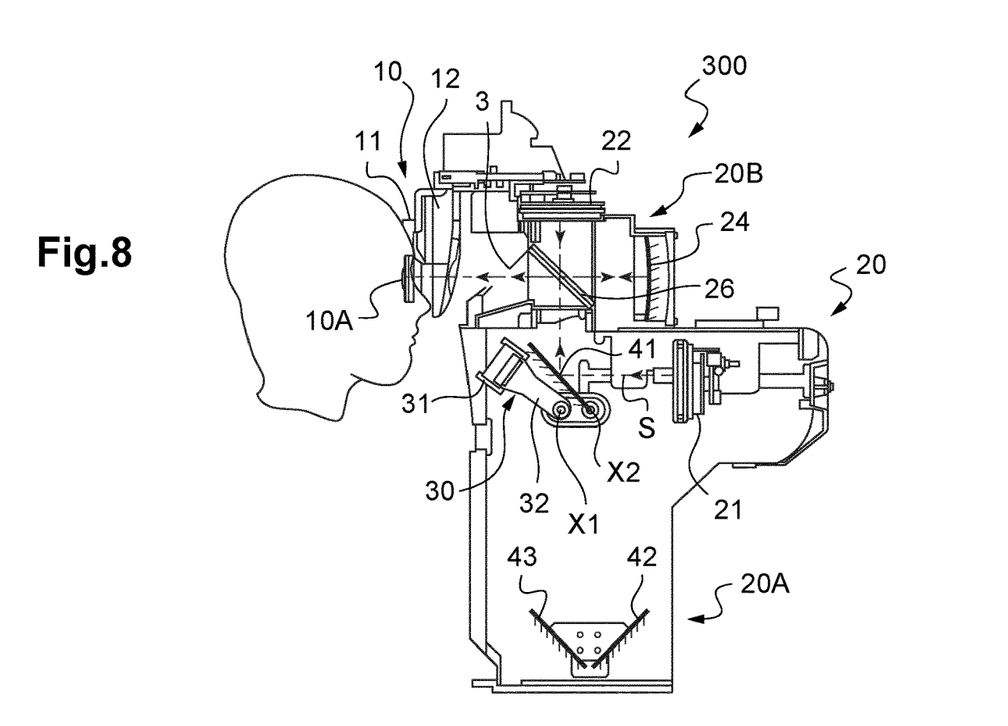

The various elements of the refraction test unit 10 (such as the variable spherical power lens, the cylindrical lenses, the motors and the control unit) are enclosed in a housing 12 shown on FIGS. 7 and 8. This housing 12 is different from the casing 2 enclosing the display unit 20. The refraction test unit 10 and the display unit 20 are housed in separated casings.

As a variant, refraction test unit and display test unit could be housed in a common casing. In a general manner however, they are located in different spatial regions of the optometry device. These different spatial regions do not overlap.

In the present embodiment, the optometry device includes two visual compensation systems as mentioned above, each such system being situated in front of one of the individual's eyes. The adjustable powers of these visual compensation systems are vision correction powers for the eye of the individual placed nearby.

The exit aperture 10A of the optometry device 100; 200; 300; 400 corresponds to opening of the refraction test unit where the individual may position his eye to look through the optical system of the refraction test unit 10, namely the phoropter or visual compensation system. This exit aperture is centered on the optical axis of the lens or lenses of the refraction test unit.

However, the exit aperture is usually off-centered relative to an optical axis of the optical elements of the display unit, as will be described in more details later.

The refraction test unit 10 optionally comprises one or more element designed to receive the head of the individual and hold it in a predetermined position relative to the refraction test unit 10. This element may for example receive the forehead of the individual, such as element 11 represented on the figures. Alternatively or in addition, the refraction test unit could comprise an element to receive the chin of the individual.

Such refraction test unit 10 is well-known and will not be described in more details here.

The light beam exiting the display unit 20 is directed through the lens or lenses of the test unit 10 towards the eye of the individual. The eye of the individual is applied against the exit aperture 10A of the test unit, through which the light beam emitted by the screen 21 exits the optometry device 100; 200; 300; 400.

The display unit 20 comprises:
  a screen 21 adapted to display a test picture used in producing said visual test image and
  at least one optical element 30 having an optical power.

According to the invention, said optical element 30 presents an active state in which it exhibits a non zero refraction power placed on an optical path of the light emitted by said screen 21 and exiting the device 100; 200; 300; 400 through said exit aperture 10, and an inactive state in which it introduces no refractive power on said optical path, in order for the visual test image to be produced at a variable distance from said exit aperture 10A.

In the embodiment shown on the figures, said optical element 30 is movable between an active position in which it is placed on an optical path of the light emitted by said screen and exiting the device through said exit aperture, and a retracted position in which it remains out of said optical path, in order for the visual test image to be produced at a variable distance from said exit aperture 10A.

The optical path is the path that a light beam emitted by the screen 21 at a center of the image displayed by the screen 21 takes in traversing the display unit 20 to reach the exit aperture 10A of the refraction test unit 10.

Said visual test image comprises either the test picture displayed by said screen 21 without influence of the optical element 30, reflected or not by a reflecting surface of the device 100; 200; 300; 400 or an image of said test picture projected by said optical element 30, reflected or not by a reflecting surface of the device.

By projected, it is meant that the image of the test picture is formed by the optical element, such as the lens. The image of the test picture formed by the lens is a virtual image of the test picture.

When the optical element is in its retracted position, the visual test image comprises the test picture displayed by said screen 21. The distance between the visual test image and the exit aperture of the refraction test unit 10 is then the distance measured along said optical path between the exit aperture and the screen 21.

When the optical element is in its active position, the visual test image comprises an image (or projection) of said test picture displayed by the screen 21 seen through the optical element 30. This image is usually a virtual image. It is located at an optical position. This optical position may for example be at infinity.

The distance between the visual test image and the exit aperture of the refraction test unit 10 is then the distance between the exit aperture and the optical position of the visual test image. Said optical element 30 may comprise for example an optical lens 31, as in the example described here.

In the case where the optical element 30 comprises an optical lens 31, the image of the test picture is the image of the test picture seen through the lens 31.

In the example described here, said optical element 30 comprises a single lens 31. This lens 31 may be a lens with fixed or variable power. It is here the only optical lens comprised in said display unit 20. It is therefore the only optical lens enclosed in said casing 2.

According to the invention, the distance between said visual test image and said exit aperture is varied at least between a distance of far vision and a different distance of near or intermediate vision. A distance of far vision is typically comprised between infinity and 65-70 centimeters. A distance of intermediate vision is typically comprised between 65-70 and 40 centimeters. A distance of near vision is typically comprised between 40 and 33 centimeters.

Preferably, the relative positions of the screen 21, the optical element 30 and the exit aperture 10A are adapted to be varied in order for said distance between the visual test image produced and the exit aperture to be continuously varied inside one or several ranges of optical distances between infinity and a near vision distance.

In another embodiment of the optometry device according to the invention, not shown on the figures, said optical element remains placed on said optical path of the light and has a variable refractive power, variable between a non zero value corresponding to said active state, and a zero value, corresponding to said inactive state.

In this other embodiment, the optical element is preferably fixed, non movable.

Except for these differences, the optometry device according to this embodiment is identical to the embodiment described in detailed hereafter.

Of course, an embodiment of the optometry device that could be used in two different ways could be considered if the optical element has a variable power and is nonetheless movable between an active position where the optical path of the light goes through the optical element and a retracted position where the optical element is out of the optical path of the light. In this case the active and inactive states of the optical element may be obtained either by physically moving the optical element or optical changing the optical power of the optical element.

Minimal Configuration of the Optometry Device:

In a minimal configuration, said visual test image may be produced at only two different distances:

1) It may be produced at a first and minimal optical distance corresponding to the optical distance between the exit aperture and the screen, defined when the optical element adopts its retracted position or inactive state, the screen 21 being observed directly by the individual. In this configuration, no optical component or only one or several reflecting surfaces are placed on the optical path between the exit aperture and the screen. The screen is directly observed by the subject, with no influence of the optical element which is in the retracted position or an inactive state. This first distance preferably corresponds to a near or intermediate vision distance (FIG. 8).

2) Said visual test image may also be produced at a second and maximum optical distance corresponding to the optical distance between the exit aperture and the virtual image of the screen, when said optical element is placed in the active state on the optical path between the exit aperture and the screen. The screen is indirectly observed by the subject, through said optical element, the subject observing the virtual image of the screen. This second distance preferably corresponds to a far vision distance. The optical element is for example positioned on said optical path in the active state in order for the exit aperture to be optically conjugated with said screen.

In this minimal configuration, it is possible to consider that the optometry device according to the invention comprises only a fixed screen and said optical element movable between the retracted and active positions in order to produce the visual test image at two different optical distances. The optical element may have a fixed power. It is also possible to consider that the optometry device according to the invention comprises only a fixed screen and said optical element is of the tunable type, i.e. with a tunable optical power varying between zero (inactive state) and non zero values (active state). The optical element may in this case have a variable power and be always kept along the optical path, only its optical power being changed from one state to the other Minimal Configuration with Reflecting Surfaces to Fold the Optical Axis A need to confer to the optometry device a compact configuration can be raised. However, the screen 21 and the optical element 30 when it is a lens, requires to be separated by an optical distance close to the focal distance of the lens, so as to be able to provide a far distance vision of the screen 21, knowing that focal distance could be set to several twenties centimeters (80-100 cm in the examples).

One or several reflecting surfaces may be used in order to fold the optical path of the light and limit the size of the display unit.

Such reflecting surfaces can be arranged so that the screen 21 and the optical element 30 both can be positioned at the nearest one another (for example at less than 20 or preferably less than 10 centimeters one another).

As such, the optical distance between the screen 21 and the optical element 30 can be set at the nearest to the focal distance of the optical element 30 and the virtual image given from the screen be observed in conditions closed to infinity (4 or 6 meters, even more). The two distances of observation are obtained respectively when the optical element is along (farthest distance of observation) and outside (nearest distance of observation) the optical path.

Enhanced Configurations with More than 2 Distances

In the above configuration, to also provide a minimal near vision distance, at least one reflecting surface can be used to short-circuit a part of the optical path allowing an observation in far distance when the optical element is in inactive state or retracted position.

To this end, in the embodiment shown on the figures, the screen 21 and the optical element 30 are arranged with their optical axis and screen axis perpendicular to one another (considering the screen 21 produces a light beam along a screen axis S perpendicular to the mean plane of the screen 21). Moreover a first reflecting surface is mounted mobile between a far/intermediate vision position wherein it directs the light coming from the screen 21 to the successive reflecting surfaces, and a near vision position, wherein it directs the light coming from the screen 21 towards the exit aperture instead of the optical element in its first active position.

Preferably, said distance between the visual test image produced and the exit aperture may take more than 2, preferably more than 3, more than 4, more than 5, values comprised between infinity and a near vision distance. To this end, the optical element may have a variable power and/or the screen may be movable in translation, continuously or step-wise along the optical path of the light emitted by it. It is also possible to provide these different distances by providing one or more movable reflecting surfaces. Each reflecting surface may either be movable in translation or in rotation. It may be movable in and out of the optical path of the light or be movable along the optical path of the light.

In one embodiment as such, the optometry device may comprise no reflecting surface 41, 42, 43 intended to fold the optical path between the screen and the optical element, the screen axis and the optical axis of the lens be aligned, and the screen 21 be defined mobile in translation along this common axis, to define several far/intermediate distances when the optical element is in the active state, and several near distances when the optical element is in the inactive state.

Preferably, said distance between the visual test image produced and the exit aperture may take any value comprised between infinity and a near vision distance. To this end, the optical element may have a variable power and/or the screen and/or one or more reflecting surfaces may be movable, in particular in translation along the optical path of the light emitted by it.

In the different embodiments represented on the figures, the optometry device 100; 200; 300; 400 according to the invention includes a casing 2 adapted to be placed on a table, for instance, or to be mounted on a stand to be placed on a table or on the floor.

The casing 2 encloses here the display unit 20. The test unit 10 is placed outside this casing 2 and preferentially mounted on the casing 2.

The display unit 20 comprises here an acuity module 20A and a scene module 20B.

The acuity module 20A includes the screen 21 and the optical element 30.

The screen 21 is for instance one of the following: a LED or OLED screen, a serigraphy with backlight screen, a display light projection screen with micro video projector, an LCD screen or a TFT screen. It produces a light beam along a screen axis S perpendicular to the mean plane of the screen 21. This light beam is meant to produce an image of an object, such as an optotype, for an individual using the optometry device.

In the examples described here, the screen 21 is flat.

The test picture displayed by the screen 21 is for example an optotype. Other types of picture adapted to test the vision of the individual may be used, as known by the man skilled in the art. The acuity module 10 is thus designed to produce visual test image (representing an object, such as an optotype) for the individual's eye.

The optical element 30 comprises here an optical lens 31. Lens 31 is here an achromatic lens, having an effective focal length between 70 centimeters and one meter, preferably of about 80 centimeters, for instance. It comprises for example an achromatic doublet. It may also be for example a simple lens. In the case where a simple lens is used, this simple lens has preferably an effective focal length of more than 80 centimeters to limit chromatic aberrations, for example 82 centimeters.

In the examples described here, the lens 31 can be of the convex type. In this case, its focal distance and its relative position with the screen 21 and the exit aperture can be determined such that the screen 21 is situated at a distance inferior or at most equal to the focal distance of the lens. As such, when the lens 31 is in an active state, i.e. along the optical path and with an optical power different from zero, it provides to the subject looking at the exit aperture, a virtual image from the screen with a bigger size (magnifying glass effect). Also, this virtual image is observed from the exit aperture by a virtual distance bigger than the optical distance existing between the exit aperture and the screen 21 when the lens is in inactive state, for example in the retracted position.

In the examples described here, when the lens 31 in the inactive state, that is, out of the optical path or with an optical power equal to zero, the minimum optical distance between the exit aperture and the screen 21 can be set at a near vision distance, for example of 40 or 33 cm (see FIG. 8).

The effective focal length of the lens 31 corresponds to the optical power of the lens itself. It is measured between a focal plane of the lens and a theoretical plane placed inside the lens. As it is not easy to position optical elements relative to the lens using the effective focal length, the position of the theoretical plane being difficult to precisely determine, a back focal length may be used.

The back focal length of the lens 31 is measured between the last dioptre's summit of the lens and the focal plane of the lens along an optical axis L of the lens 31, that is to say from the back surface of the lens to the focal plane of the lens 31.

As explained later, the optical axis L is here folded by the use of reflective surfaces such as mirrors.

Alternatively, the use of lenses with a small effective focal length, for example 20 centimeters, is possible with a smaller screen such as a miniature screen of 1 inch with high resolution HD or full HD. This could be used for obtaining a smaller device.

Preferably, the optical element 30 and the screen 21 are arranged relative to each other so that there is at least one relative position of the optical lens 31 and the screen 21 for which the screen 21 is placed at a distance from the optical lens 31 equal to the back focal length of said lens 31.

Therefore, in a far vision configuration, while the lens 31 is placed on the optical path of the light, the relative position of said screen 21 and said lens 31 may be adjusted for the screen 21 to be located at a back focal length from said lens 31.

This way, the visual test image generated by the display module 20 may be placed at infinity relative to the exit aperture, and therefore, the eyes of the individual. The distance between the visual test image produced and the exit aperture is then set as infinite.

According to an embodiment of the invention, the optical element 30 is movable between at least said first active position where the optical path of the light beam emitted by the screen 21 and travelling to the eye of the individual goes through the optical element 30, and said second retracted position where the optical path of this light beam avoids the optical element 30. In the case of the optical element 30 being a lens 31, the light beam goes through the lens 31 when it is in the active position and does not go through the optical lens 31 when it is in the retracted position.

Thanks to this, the acuity module is adapted to produce the image of the object at a variable distance for the individual's eye.

In practice, here, in all the described embodiments, the optical element 30 comprises the lens 31. It is fixed on a support 32 that is pivotally mounted on part of the casing 2 of the device 100; 200; 300; 400.

In a first angular position of the support 32 of the lens 31, shown for example on FIGS. 1, 4, 7 and 9, the support 32 is parallel to the optical path of the light and brings the lens 31 across this optical path: the light emitted by the screen then goes through the lens 31. The optical path of the light follows at least partially the optical axis L of the lens 31.

In a second angular position of the support 32 of the lens 31, shown for example on FIGS. 2, 3, 5, 6 and 8, the support 32 is inclined relative to the optical path of the light and brings the lens 31 outside this optical path: the light beam emitted by the screen 21 then avoids going through the lens 31.

Of course, the geometry of the support 32 allows it to remain out of the optical path at all angular position of this support 32.

The support 32 is pivotally mounted in order to be able to pivot about a rotation axis X1 perpendicular to the optical path of the light beam at the position of the lens 31 when it is place in the first angular position. In other words, the rotation axis of the lens 31 is perpendicular to the optical axis L of the lens 31.

In the example described here, the lens 31 is of rectangular shape. It is inserted inside a frame that surrounds its edge. Two triangular branches link the frame to the pivot axis of the lens 31. A rectangular ring keeps the lens 31 in place in the frame. This ring is mounted thanks to screws on the sides of the frame facing the pivot axis.

In all embodiments described here, said screen 21 is movable in translation along two perpendicular directions for centering said screen 21 relative to the other optical component of the optometry device 100; 200; 300; 400, in particular relative to the optical axis L of said lens 31 in its active position or state.

To this effect, adjustment devices for centering the screen 21 relative to the optical axis L or the optical center of the lens 31 when in its active position or state are provided. In other words, the adjustment devices allow optically centering the screen 21 on the optical axis L of the lens 31. These adjustment devices comprise an adjustable support 23 for the screen 21. This adjustable support 23 may be moved in a plane parallel to the screen 21. This plane is, in practice, perpendicular to the screen axis S. This adjustment is made during manufacturing. It may optionally be repeated during the life of the device. The movements of the screen in this plane may be achieved manually, for example with micrometer screws, or automatically through a motorized system controlled by an electronic unit (not represented on the figures).

Motorized active recentering of the screen 21 may be implemented. Alternatively, the screen may be centered for predetermined fixed positions only.

Thanks to the adjustment devices, the screen 21 is accurately centered relative to the optical center of the lens 31. This centering step ensures that the light emitted at the center of the screen exits the optometry device at the center of the exit aperture.

The size of the mirrors and lens is chosen to be wide enough to enable easy centering of the visual test image. The minimal distances between screen, mirrors and lens may also be enlarged to facilitate this centering.

Moreover, in addition to this physical centering of the screen, a numerical centering correction may be applied to the test picture displayed by the screen 21 in order to compensate predetermined deviation of the screen or other optical component, in particular the reflecting surfaces in predetermined configurations of the device. This numerical centering correction consists in shifting the test picture on the screen in order for it to appear centered relative to the exit aperture. The electronic unit may be programmed to implement this correction of the test picture.

The physical and numerical centering adjustments aim at maintaining said visual test image visible for the eye of the individual through the exit aperture of the device centered for all relative positions of the optical components of the device.

Thanks to the adjustment devices, the image displayed by the screen may be accurately centered relative to the optical axis L of the lens 31.

When the screen 31 and/or image displayed by the screen is accurately centered on the optical axis L of the lens 31, the screen axis considered at the center of the image displayed, the optical axis L of the lens 31 and the optical path of the light coincide inside the display unit.

Between the display unit 20 and the test unit 10, the optical path of the light may deviate from the optical axis L of the lens 31, as the test unit 10 and thus the exit aperture 10A are placed on front of the eye of the individual and may therefore be shifted relative to the optical axis L of the lens 31.

As described in more details later, in some embodiments the screen 21 may also be movable, in particular along the screen axis S, in order to further vary the distance between the visual test image and the exit aperture.

In such embodiments (see first and second embodiments) said screen 21 of the acuity module 20A is movable in translation along a reference axis between two positions corresponding to different distances between the visual test image and the exit aperture. This reference axis is here overlapped or parallel with the screen axis S.

In the embodiments described in more details hereafter, the acuity module 20A of the display unit 20 also comprises at least one reflecting surface. Said reflecting surface is arranged in said device 100; 200; 300; 400 in order to direct the optical path toward the exit aperture 10A.

Said reflecting surface allows folding the optical path of the light beam emitted by the screen, in order to limit the size of the display module.

In practice, said at least one reflecting surface comprises at least one mirror, preferably between two and four mirrors.

Alternatively, said reflecting surface may comprise any kind of beam splitter.

Alternatively, in a simplified embodiment, said optometry device may comprise no reflecting surface. As in the embodiments described here, the screen is then placed on the optical axis of the lens, and preferably movable in translation along the optical axis of the lens. The optical axis of the lens is then straight, as it is not folded by the mirrors.

Moreover, said at least one reflecting surface may be movable in translation and/or in rotation between at least two positions.

The reflecting surface may be movable in order to further vary the distance between the visual test image and the exit aperture, as will be described in more details later.

The scene module 20B comprises here an additional screen 22 and an additional mirror 24. The additional screen 22 is used to display a background picture. This background picture is preferably of an environment familiar to the individual, for example a natural environment, exterior or interior, such as a city, a landscape or a room. The additional mirror 24 is here a concave mirror. Its optical axis goes through the summit of the concave mirror and is here overlapped with the optical axis L of the lens 31 of the acuity module 20A at the exit from the display unit.

The additional screen 22 may be a video display, for instance an LCD display, or any adapted screen of the type described earlier in reference with the screen 21 of the acuity module 20A.

In a variant, the additional screen may comprise a LED matrix and a light-diffusing device. The LED matrix is placed behind the light-diffusing device in order to produce a soft ambient light that will surround the visual test image produced by the acuity module.

A beam splitter 26 is place between the acuity module 20A and the scene module 20B in order to superimpose the light emitted by the screen 21 of the acuity module 20A and the light emitted by the additional screen 22 of the scene module 20B. The beam splitter 26 is positioned such that it reflects the light coming from the screen 21 of the acuity module 20A towards the refraction test unit 10 and, ultimately, towards the eye of the individual. It also reflects the light emitted by the additional screen 22 towards the additional mirror 24 and let the light reflected by this additional mirror 26 go straight through it towards the eye of the individual. Both light beams, coming from the acuity and scene modules exit the casing 2 of the display module through an opening 3.

The exemplary embodiments shown on the figures will now be described in more details.

Figure 1:
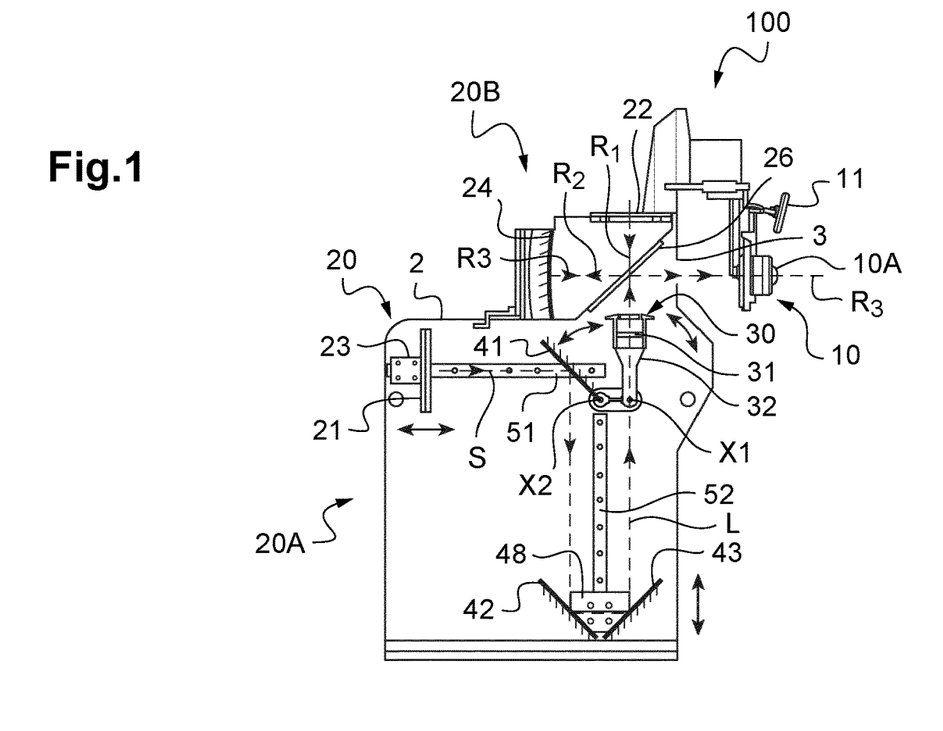
FIGS. 1 to 3 relate to a first embodiment of the invention.
Figure 2:
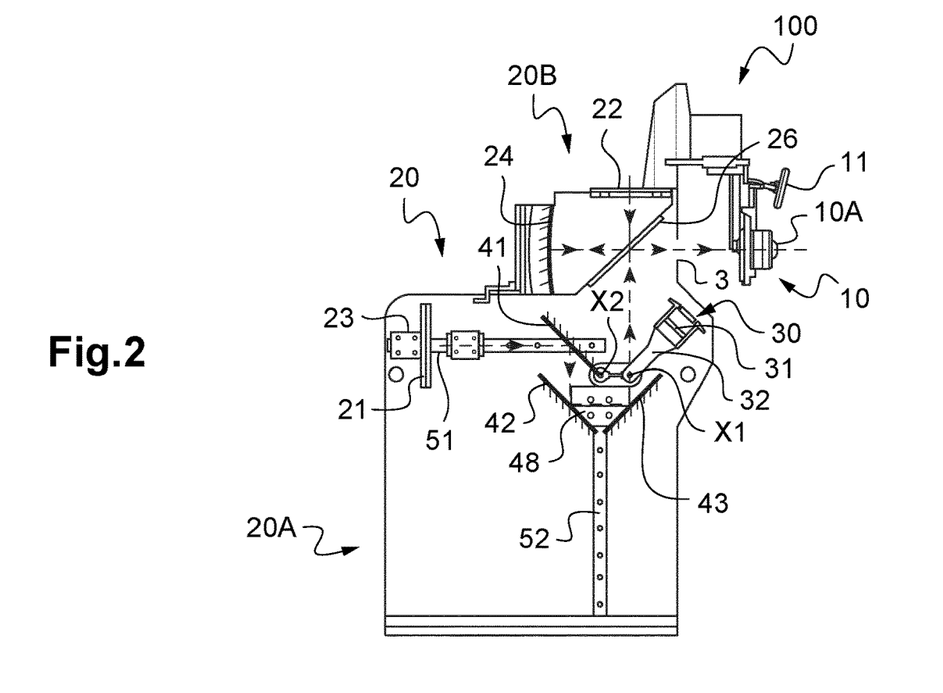
Figure 3:
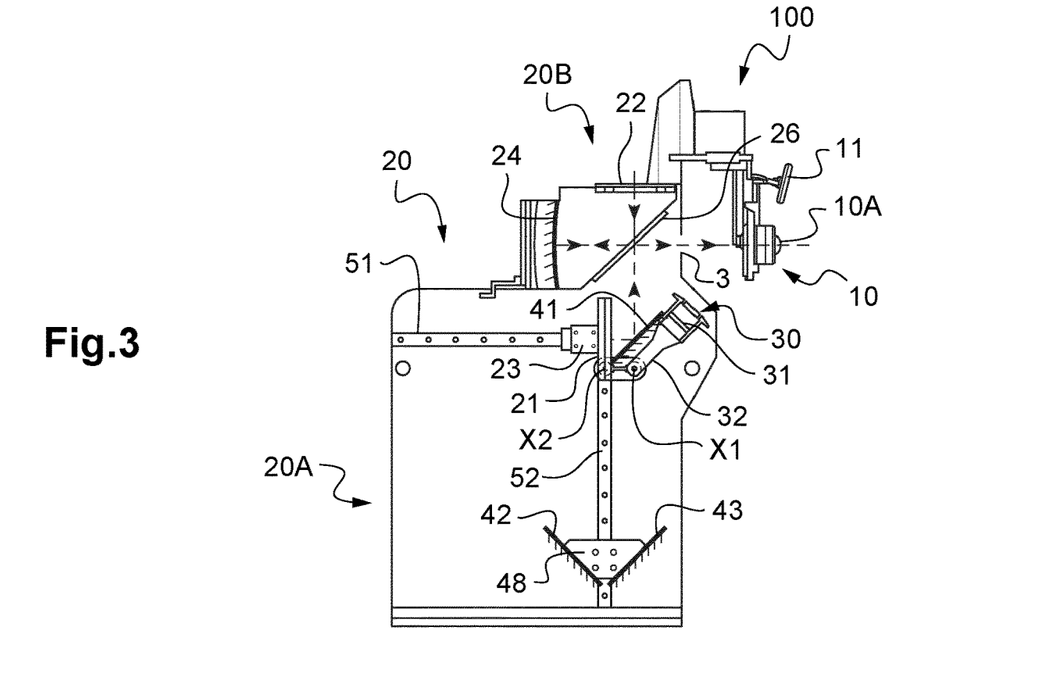

The first embodiment, shown on FIGS. 1 to 3, is a sophisticated embodiment.

In this first embodiment, the acuity module 20A comprises three mirrors 41, 42, 43. The screen axis S is here horizontal. The main direction of the optical axis L of the lens 31 in its active position or state is here vertical outside the portion of the optical axis L folded by mirrors.

A first mirror 41 is placed on the screen axis S. It is movable to pivot about a rotation axis X2 perpendicular to the screen axis S. In a first position, the first mirror 41 is oriented at 45° to the screen axis S and reflects the light beam emitted by the screen 21 towards a second mirror 42 (FIGS. 1 and 2), and in a second position, it is oriented at 135° to the screen axis S and reflects the light beam towards the beam splitter 26 (FIG. 3). The second position of the first mirror 41 may only be reached when the optical element 30 is in its retracted second position.

Second and third mirrors 42, 43 are disposed at a right angle with respect to each other. In addition, they are disposed at angles of 45° and 135°, with respect to the screen axis S.

Thanks to this arrangement, while the first mirror 41 is in its first position, the light beam produced by the screen 21 may be successively reflected by the first mirror 41 towards the second mirror 42. It is then reflected by the second mirror 42 towards the third mirror 43, then by the third mirror 43, such that it is directed towards the lens 31 along the optical axis L of the lens 31. The screen axis S and said main direction of the optical axis L are here perpendicular to each other.

The light beam goes through the lens 31 (when the optical element 30 is in the first active position) then reaches the beam splitter 26 and is reflected towards the eye of the individual.

In this first embodiment, the support 23 of the screen 21 is movable along the screen axis S. It is indeed for example adapted to slide on a first rail 51 mounted on the casing 2 parallel to the screen axis S. The distance between the visual test image and the exit aperture may thus be modified by moving the screen 21. The movement of the screen 21 may be visualized on the figures by comparing FIGS. 2 and 3. On FIG. 2, the screen 21 is further away from the first mirror 41 and the optical element 30 than on FIG. 3.

In addition, second and third mirrors 42, 43 are held together on a base 48 which is mounted on a rail 52 of the acuity module 20A such that mirrors 42, 43 are slidably movable parallel to the main direction of the optical axis L of the lens 31.

By moving the base 48 carrying mirrors 42, 43 (for instance thanks to an electric motor and associated mechanism, which are not shown on the figures), the distance between the visual test image produced and the exit aperture can be further modified.

The movement of the mirrors 42, 43 may be visualized on the figures by comparing FIGS. 1 and 2. On FIG. 1, the mirrors 42, 43 are further away from the optical element 30 than on FIG. 2.

Thanks to this, the acuity module 20A is adapted to produce the visual test image at a variable distance for the individual's eye E.

The lens 31 has here for example an effective focal length of 823 millimeters with 10% accuracy. The back focal length is here 813 millimeters.

On FIG. 1, the lens 31 is in the first active position. The first mirror 41 is in the first position, the second and third mirrors are in their extreme position furthest away from the lens 31. The screen 21 is also in an extreme position where it is placed furthest away from the first mirror 41 in its first position.

The different elements of the device are arranged such that in the configuration shown on FIG. 1, the screen 21 is placed in the focal plane of the lens. The test picture displayed on said screen therefore appears to be at an infinite distance from the eye of the individual. The distance between the visual test image and the exit aperture is therefore infinite. The vision of the eye of the individual may therefore be tested in far vision conditions, by assessing the visual performance of the individual observing said visual test image.

The second and third mirrors 42, 43 may then be slid from the extreme position shown on FIG. 1 to another extreme position closest to the optical element 30.

By moving the second and third mirrors 42, 43 along the second rail 52 while the screen 21 remains in the extreme position of FIG. 1, and moving the lens 31 from its active to its retracted position, the distance between the visual test image produced and the exit aperture 10A may be varied from infinity to about 68 centimeters. The vision of the eye of the individual may therefore be tested in far vision conditions for any distance comprised between infinity and 68 centimeters.

As the mirrors 42, 43 may here be slid continuously on the second rail 52, the distance between the visual test image and exit aperture may also be varied continuously in the range between infinity and 68 centimeters.

The field of view along the horizontal axis of the screen 21 is about 8°. The maximum acuity determined is 20/10 based on the fact that standard optotypes require a minimum of two pixels to form the inside shape of said optotype according to the norm PR NF EN ISO 10938 and NF EN ISO 8596.

Alternatively, the screen 21 may also be slid from the extreme position shown on FIG. 1 to an intermediate position (not represented on the figures), where it is closest to the first mirror 41 in its first position.

The corresponding distance between the visual test image and the exit aperture may then be varied between 5.6 meters to infinity when moving only the screen and between 1 meter to infinity when moving only the second and third mirrors 42, 43 between their two extreme positions.

Alternatively, the screen and mirrors may be positioned in order to produce a visual test image located at 6 meters from the exit aperture 10A and the visual performance of the eye of the individual may be evaluated at 6 meters. This measurement may allow calculating the visual performance for an optotype placed at infinity, for example by adding a spherical offset to the spherical correction measured. More precisely, acuity measured at 6 meters can be converted to an acuity measured at infinity by adding an offset of +0.16 diopter, as it is known in the field.

In the configuration shown on FIG. 2 of the first embodiment, the optical element 30 comprising the lens 31 is in its second retracted position. The distance between the visual test image and exit aperture is about 67 centimeters.

The screen 21 may then be slid from the extreme position shown on FIG. 1 to an intermediate position (not represented on the figures), where it is closest to the first mirror 41 in its first position.

The second and third mirrors 42, 43 may also be slid between the extreme position shown on FIG. 1 and said another extreme position closest to the optical element 30.

By moving the screen 21 along the first rail 51 and the second and third mirrors 42, 43 along the second rail 52, the distance between the visual test image and the exit aperture may be varied from about one meter to about 50 centimeters. The vision of the eye of the individual may therefore be tested in intermediate vision conditions for any distance comprised between one meter and 50 centimeters.

As the screen 21 and mirrors 42, 43 may here be slid continuously on the first rail 51 and second rail 52, respectively, the distance between the visual test image and the exit aperture may also be varied continuously in the range between one meter and 50 centimeters.

The field of view of the screen 21 is then about 8°. The maximum acuity determined is 10/10 based on the fact that standard optotypes require a minimum of two pixels to form the inside shape of an optotype.

In the configuration of FIG. 3 of the first embodiment, the optical element 30 is still in the retracted position, and the first mirror 41 is in the second position, pivoted toward the optical element. In this configuration, the light beam is reflected directly from the screen 21 to the beam splitter 26 by the first mirror 41, without being reflected by the second and third mirrors 42, 43. Only the screen 21 may be moved to vary the optical position of the visual test image, and therefore the distance between the visual test image produced and the exit aperture. The second and third mirrors 42, 43 are by-passed. The configuration of FIG. 3 corresponds here to a distance between said visual test image and exit aperture of 33 centimeters.

By moving the screen 21 along the first rail 51 the distance between the visual test image produced and the exit aperture may be varied from about 50 to about 33 centimeters. The vision of the eye of the individual may therefore be tested in near vision conditions for any distance comprised between 50 and 33 centimeters.

As the screen 21 may here be slid continuously on the first rail 51, the distance between the visual test image produced and the exit aperture may also be varied continuously in the range between 50 and 33 centimeters. When the screen is slid between its two extreme positions on the first rail 51, the field of view of the screen 21 varies between 12 and 15°.

The screen 21 and the three mirrors 41, 42, 43 are controlled to move for instance thanks to an electric motor 19 and associated mechanism, which are not shown in the figures.

The setpoint for the position of the screen and mirrors may be automatically determined by a software taking into account the visual performance of the eyes of the individual in identifying the optoptype of the visual test image produced by the device.

Figure 4:
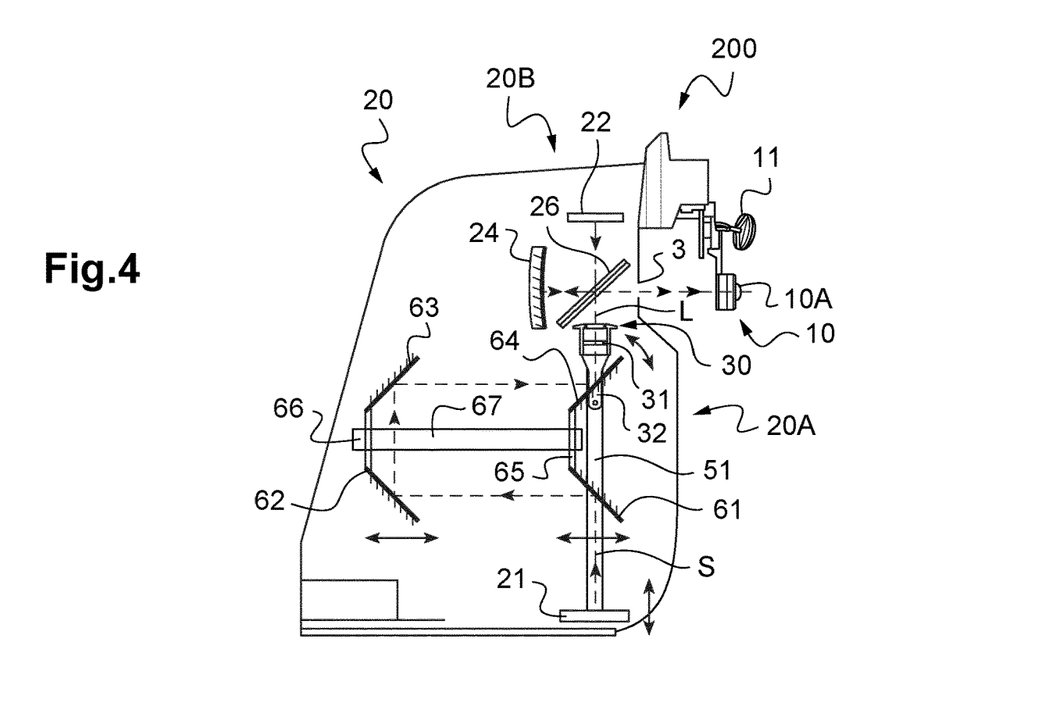
FIGS. 4 to 6 relate to a second embodiment of the invention.
Figure 5:
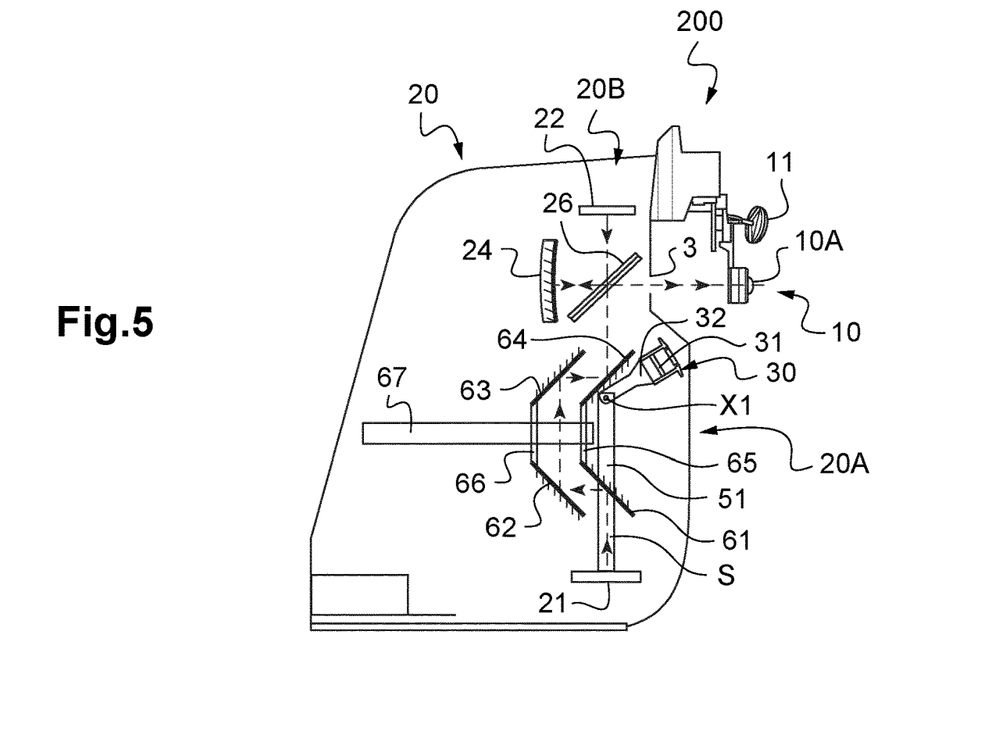
Figure 6:
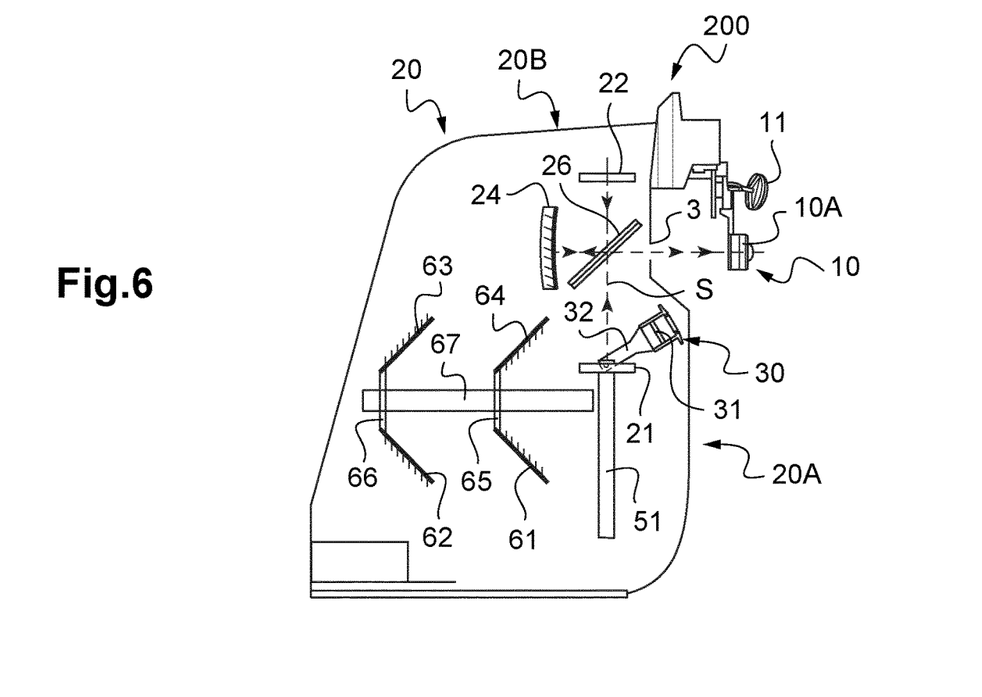

The second embodiment, shown on FIGS. 4 to 6, is also a sophisticated embodiment.

The screen axis S is vertical, as is the main direction of the optical axis L of the lens 31 in its active position. Preferably, the optical axis L of the lens 31 and screen axis S are partly overlapped. In this second embodiment, the support 23 of the screen 21 is also movable along the screen axis S. It is indeed adapted to slide on a first rail 51 mounted on the casing 2 parallel to the screen axis S. The distance between the visual test image produced and the exit aperture may thus be modified by moving the screen 21. The movement of the screen 21 may be visualized on the figures by comparing FIGS. 5 and 6. On FIG. 5, the screen 21 is further away from the optical element 30 than on FIG. 6.

In this second embodiment, the acuity module 20A comprises four mirrors 61, 62, 63, 64.

They are here held together in pairs of two mirrors oriented at right angle to each other. Each pair of a first and a second pair of mirrors is supported by an element of support 65, 66 slidably mounted on a second rail 67.

Each pair of mirrors may independently slide along the second rail 67.

In particular, the first pair of mirrors 61, 64 may be slid in and out of the screen axis S.

When the first pair of mirror 61, 64 is placed on the screen axis S, a first mirror 61 of a first pair of mirrors is placed on the screen axis S, in front of the screen 21. The first mirror 61 is oriented at 45° to the screen axis S and reflects the light beam emitted by the screen 21 towards a second mirror 62 of the second pair of mirrors, which is oriented parallel to the first mirror 61. This second mirror 62 reflects the light beam toward a third mirror 63 of said second pair of mirrors, oriented at 90° relative to the second mirror 62. The third mirror 63 reflects the light beam towards a fourth mirror 64 belonging to the first pair of mirrors, and oriented parallel to the third mirror 63.

The fourth mirror 64 reflects the light beam in a vertical direction, along the main direction of the optical axis L of the lens 31, towards the beam splitter 26.

Thanks to this arrangement, while the first pairs of mirrors 61, 64 is placed on the screen axis S, the light beam emitted by the screen 21 may be successively reflected by the first mirror 61 towards the second mirror 62. It is then reflected by the second mirror 62 towards the third mirror 63, then by the third mirror 63 towards the fourth mirror 64, and by the fourth mirror 64 towards the lens 31 along the main direction of the optical axis L of the lens 31. The screen axis S and the optical axis L are here partly overlapped.

The light beam goes through the lens 31 (when the optical element 30 is in the first active position) then reaches the beam splitter 26 and is reflected towards the eye of the individual.

When the first pair of mirrors is placed on the optical path, the distance between the visual test image and the exit aperture 10A can be modified, by moving the base 66 carrying the second pair of mirrors 62, 63 (for instance thanks to an electric motor and associated mechanism, which are not shown on the figures) relative to the base 65 of the first pair of mirrors 61, 64.

The movement of the second pair of mirrors 62, 63 may be visualized on the figures by comparing FIGS. 4 and 5. On FIG. 4, the mirrors 62, 63 of the second pair of mirrors are further away from the mirrors 61, 64 of the first pair of mirrors and from the optical element 30 than on FIG. 5.

On FIG. 4, the lens 31 is in the first active position. This lens has for example an effective focal length of 857 millimeters. The first pair of mirrors 61, 64 is placed on the optical path of the light emitted by the screen 21; the second pair of mirrors 62, 63 is in its extreme position furthest away from the first pair of mirrors 61, 64. The screen 21 is also in an extreme position where it is placed furthest away from the first mirror 61 of the first pair of mirrors.

The different elements of the device are arranged such that in the configuration shown on FIG. 4, the screen 21 is placed in the focal plane of the lens 31. The image of the test picture displayed on said screen therefore appears to be at an infinite distance from the eye of the individual. The distance between the visual test image and the exit aperture 10A is therefore infinite. The vision of the eye of the individual may therefore be tested in far vision conditions, by assessing the visual performance of the individual observing said visual test image.

The field of view of the screen 21 is about 9°. The maximum acuity determined is 16/10 based on the fact that standard optotypes used require a minimum of 2 pixels to form the inside shape of a letter.

The screen 21 may then be slid from the extreme position shown on FIG. 4 to an intermediate position, where it is closer to the first mirror 61 of the first pair of mirrors while placed on the optical path of the light beam, as seen on FIG. 5.

The second pair of mirrors 62, 63 may also be slid from the extreme position shown on FIG. 4 to another extreme position closest to the first pair of mirrors 61, 64.

By moving the screen 21 along the first rail and the second pair of mirrors 62, 63 along the second rail 67, the distance between the visual test image and the exit aperture 10A may be varied from infinity to about 2 centimeters. The vision of the eye of the individual may therefore be tested in far vision conditions for any distance comprised between infinity and 2 centimeters.

As the screen 21 and mirrors may here be slid continuously on the first rail and second rail 67, respectively, the distance between the visual test image produced and the exit aperture may also be varied continuously in the range between infinity and 1.5 centimeters.

In the configuration shown on FIG. 5, the optical element 30 comprising the lens 31 is in its second retracted position.

The screen 21 may be slid from the extreme position shown on FIG. 4 to a position (not represented on the figures), where it is closest to the first mirror 61 of the first pair of mirrors (on the optical path).

The second pair of mirrors 62, 63 may also be slid from the extreme position shown on FIG. 4 to said another extreme position closest to the first pair of mirrors.

Thereby, the distance between the visual test image and the exit aperture 10A may be continuously varied from about 70 centimeters to about one meter.

The vision of the eye of the individual may therefore be tested in intermediate vision conditions for any distance comprised in this range.

The configuration shown on FIG. 5 corresponds to a distance between the visual test image and exit aperture of 67 centimeters.

In the configuration of FIG. 6, the optical element 30 is still in the retracted position, and the first and second pairs of mirrors 61, 62, 63, 64 are slid to be placed out of the optical path of the light emitted by the screen 21.

In this configuration, the light beam is directed from the screen 21 to the beam splitter 26 without being reflected by any mirror. Only the screen 21 may be moved to vary the length of the optical path in this configuration. The first and second pairs of mirrors are by-passed.

By moving the screen 21 along the first rail, the distance between the visual test image and the exit aperture 10A may be varied from about 50 to about 25 centimeters. The vision of the eye of the individual may therefore be tested in near vision conditions for any distance comprised between 50 and 25 centimeters.

The configuration shown on FIG. 6 corresponds to a distance between the visual test image and exit aperture of 33 centimeters.

As the screen 21 may here be slid continuously on the first rail, the distance between the visual test image produced and the exit aperture may also be varied continuously in the range between 50 and 33 centimeters.

The screen 21, mirrors 61, 62, 63, 64 and optical element 30 are controlled to move for instance thanks to an electric motor and associated mechanism, which are not shown in the figures.

The third embodiment shown on FIGS. 7 and 8 is a simplified variant of the first embodiment described previously.

In this third embodiment, the acuity module comprises optical components that are similar to those of the first embodiment, except that the screen 21 and the second and third mirrors 42, 43 are fixed and not mobile.

As in the first embodiment, the first mirror 41 is placed on the optical path and mounted to pivot about a rotation axis perpendicular to the optical path of the light beam, in order to be alternatively placed at an angle of 45° or 135° relative to the screen axis S.

In this embodiment, the light emitted by the screen may follow one of three optical paths, depending on the angular position of the first mirror 41.

When the first mirror 41 is in the first position (45° to the screen axis S), and the optical element 30 is in its active position (FIG. 7), the light is reflected by the first mirror 41, towards the second mirror 42, and by the second mirror 42 towards the third mirror 43, and by the third mirror towards the optical element 30 and the beam splitter 26. The distance between the visual test image produced and the exit aperture is then about 6 meters: the test picture displayed by the screen 21 is then seen at a distance of about 6 meters by the eye of the individual.

With no other modification, the optical element 30 may be pivoted to its retracted position. The distance between the visual test image and the exit aperture 10A is then about one meter.

The first mirror 41 may then be pivoted to its second position (135° to the screen axis S). The light beam emitted by the screen 21 is then reflected by the first mirror 41 directly towards the beam splitter 26 and then reflected by the beam splitter 26 towards the eye of the individual. The distance between the visual test image and the exit aperture 10A is then about 40 centimeters (in the configuration of FIG. 8).

The visual test image may therefore be displayed at three fixed distances from the exit aperture of the device.

With the third embodiment of the optometry device 300, the visual test image may be observed at three different optical distances by the individual.

The fourth embodiment is another simplified variant of the first embodiment. In this fourth embodiment, represented on FIG. 9, the screen is fixed. The screen axis S is vertical and the first mirror 41 is removed. The second and third mirror 42, 43 are mounted to be slidable vertically along a second rail 52 similar to the first embodiment.

Figure 9:
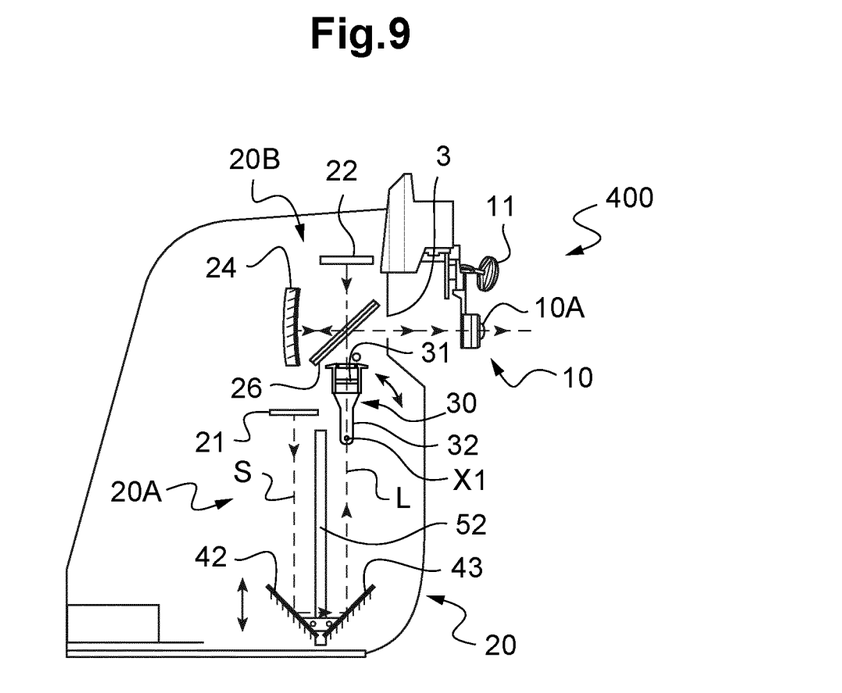
FIG. 9 relates to a fourth embodiment of the invention.

The light beam emitted by the screen 21 is directly emitted towards the second mirror 42, reflected by the second mirror 42 towards the third mirror 43, and reflected by the third mirror 43 towards the optical element 30 in its active position, or towards the beam splitter 26 when the optical element 30 is in the retracted position.

The lens 31 has here for example an effective focal length of 686 millimeters. The field of view of the screen 21 is then about 11° along the horizontal axis. The maximal acuity determined is 16/10 at 2 pixels. The size of the pixel is for example about 63 microns.

With the lens in the active position, the distance between the visual test image and the exit aperture 10A may be varied in the range: 80 centimeters to infinity.

With the lens in the retracted position, the distance between the visual test image and the exit aperture 10A may be varied in the range 40 to 95 centimeters.

With the fourth embodiment of the optometry device 400, the visual test image may be observed in two different ranges of distances by the individual.

In practice, no matter which embodiment is considered, the movements of translation of the screen along to the optical path of the light emitted by the screen and/or the movements of rotation or translation of the mirrors and/or the movement of the optical element of the acuity module are preferably achieved automatically through a motorized system controlled by said electronic unit (not represented on the figures).

The electronic unit is programmed to command these movements based on predetermined refraction process steps and parameters input by an operator.

The acuity module is adapted to produce the image of an object at a variable distance for the individual's eye E. The image of the object is a real or virtual image of the test picture displayed by the screen 21.

The field of view of the individual is large enough to observe the whole screen 21.

The light beam emerging from the acuity module 20A is ultimately reflected by the beam splitter 26 towards the test unit 10 and towards the eye of the individual through this test unit 10.

In the scene module 20B, a light beam produced by the additional screen 22 is reflected towards the additional mirror 24 by the beam splitter 26 (as shown e.g. by ray $R_1$ in FIG. 1), reflects on the additional mirror 24 towards the beam splitter 26 (ray $R_2$) and is transmitted by the beam splitter 26 so as to be eventually towards the individual's eye E (ray $R_3$).

The additional mirror 24 has a focal length making it possible for the individual using the optometry device to view the image generated by the additional screen 22 at a distance larger than 5 meters or larger than 6 meters.

Therefore, in the present embodiment, elements of the scene module 20B are positioned such that the virtual image produced by the additional screen 22 of the scene module 20B is in the distance for the individual's eye, that is to say, corresponds to distance vision for the individual.

The beam splitter 26 thus not only makes it possible to reflect the light beam produced by the acuity module 20A, but also to add in the same direction the light beam initially produced by the additional screen 22 of the scene module 20B, i.e. to combine the image produced by the acuity module 20A with another image generated by the screen of the scene module 20B. Finally, the overall image produced by the display unit and seen by the individual comprises the overlapped visual test image produced by the acuity module and scene image produced by the scene module.

In said variant where the additional screen comprises a LED matrix and a light-diffusing device, the soft ambient light produced by the scene module surrounds the visual test image produced by the acuity module.

The width of the additional screen 22 of the scene module 20B makes it possible to generate a light beam which extends substantially along the whole length of the beam splitter 26 and which is therefore visible from the individual's eye E over a rather wide angle, generally an angle of 10° or more, preferably an angle of 30° or more.

Thanks to the invention, the light beam emitted by the screen 21 of the acuity module 20A is also visible from the individual's eye E over a rather wide angle, generally an angle of 5° or more. In other words, the angular size of the visual test image measured as seen from the exit aperture 10A is over 5°, for example comprised between 5 and 25°, more preferably between 8 and 15° for the screen used for acuity test, the image of the latter being surrounded by the image of the additional screen 22 which have a wider field of view of 33° in horizontal axis.

The new optometry device 100; 200; 300; 400 according to the invention allows assessing easily the visual performance of the individual at different distances from a visual test image.

Moreover, the optical element may be removed from the optical path of the light for displaying the visual test image at a near vision distance from the eye of the individual. This allows displaying the visual test image with a bigger size of image in near vision conditions. The bigger size of image makes it possible to display a text to read and to center more easily the image with the exit aperture of the device. For example, the visual test image has an angular size of 15° along the horizontal axis when displayed at 33 centimeters when the lens 31 is in the retracted position.

A subjective refraction test using the refraction test unit 10 can thus be carried out with optotypes placed at a chosen set of different distances from the individual's eye.

This leads to more accurate refraction measurements that may include measurement at infinity using the embodiments where continuous variation of the distance between the visual test image produced and the exit aperture is possible.

While the distance between the visual test image and the exit aperture 10A is varied, the size of the optotypes, or any other object, displayed by this screen 21 may be adjusted depending on this distance. This adjustment is controlled by the electronic unit.

The optometry device described above, although being compact, can simulate real situations thanks to the image generated by the scene module with a broad field of vision. This allows performing a visual test with a visual test image close to realistic vision conditions.

By simultaneous use of the acuity module 20A and of the scene module 20B, a high resolution optotype may be displayed in the centre of an image having a broad field of vision.

When the additional screen 22 of the scene module 20B is a video display, the test performed using the optometry device can even simulate a moving environment, as in a real situation.

In the examples described here, the optical element 30 comprises an optical lens 31.

In the examples described here, the optical element 30 is movable in rotation and between said active position and said retracted position. Alternatively, the optical element may be movable in translation between said active position and said retracted position. The examples described above may for example be implemented with an optical lens movable in translation between a first position where the lens is placed across the optical path, its optical axis aligned on said main direction, and a second position where the lens is shifted out of the optical path, its optical axis remaining parallel to said main direction.

In an alternative simplified embodiment of the invention, the acuity module of the display unit does not comprise any reflecting surface, only the screen and the optical element. The screen may be movable in translation along the screen axis or not.

Moreover, the relative position and orientation of the optical component, in particular the reflecting surfaces of the device, may be modified to obtain the same distances between the visual test image and the exit aperture.

In an alternative simplified embodiment of the invention, no scene module is present.

An advantage for the embodiments using an optical element with variable power, and for the embodiments where the optical axis extends along a straight line between the optical element 30 and the screen 21, with a movable screen 21 and no folding mirrors 41, 42, 43, is to present to the subject images shown at variable distances with a seamless transition. This is possible, in the first case, because the change of power of the tunable lens is continuous, and, in the second case, because the displacement in translation of the screen 21 may also be continuous.

According to the invention, the optometry device described above may be used for testing an individual's eye, with the following steps:
i) producing a visual test image for the individual's eye based on said test picture, said visual test image being visible through an exit aperture of the optometry device, for example, a phoropter, through which the individual's eye may look at said test visual image,
ii) varying said variable distance between said visual test image and said exit aperture (10A), by changing the state of said optical element (30) between said active state and said inactive state,
iii) assessing the visual perception of said visual test image by at least one eye of the individual at different distances between said visual test image and said exit aperture.

In particular, step ii) may comprise varying a distance between said visual test image and said exit aperture, by moving said optical element between an active position in which it is placed on an optical path of the light emitted by said screen and exiting the device through said exit aperture, and a retracted position in which it remains out of said optical path.

Step ii) may alternatively comprise changing the variable refractive power of the optical element, between a non zero value corresponding to said active state, and a zero value, corresponding to said inactive state. In this case, the optical element is not moved. It remains on the optical path of the light.

The visual perception of the visual test image is assessed by asking the individual to characterize his perception of the visual test image, by saying if it is seen or not seen, or by recognizing or not an optotype such as a letter. The visual perception may also be assessed, for example, by determining the delay needed by the individual to recognize an optotype. The assessment of the visual perception may be done by any method known from the man skilled in the art.

Further, at fixed screen and optical elements positions, the optical power of the lenses in the optometry device and/or the visual test image are changed depending on the responses of the individual during the assessment step.

The invention claimed is:

1. An optometry device for testing an eye of an individual, the device comprising:
   a refraction test unit having an optical system for providing different vision correction powers close to the eye of the individual, and
   a display to produce a visual test image for the eye of the individual, said visual test image being visible through an exit aperture of test unit of the optometry device,
   the display comprising:
      a screen to display a test picture used in producing said visual test image; and
      at least one optical element having an optical power, and
   said at least one optical element presenting an active state in which the at least one optical element exhibits a non-zero refraction power and is placed on an optical path of the light emitted by said screen and exiting the device through said exit aperture, and an inactive state in which the at least one optical element introduces no refractive power on said optical path, in order for the visual test image to be produced at a variable distance from said exit aperture.

2. The optometry device according to claim 1, wherein said at least one optical element is movable between an active position, corresponding to said active state, in which the at least one optical element is placed on said optical path of the light emitted by said screen and exiting the device through said exit aperture, and a retracted position, corresponding to said inactive state, in which the at least one optical element remains out of said optical path.

3. The optometry device according to claim 1, wherein said at least one optical element remains placed on said optical path of the light and has a variable refractive power, variable between a non-zero value corresponding to said active state, and a zero value, corresponding to said inactive state.

4. The optometry device according to claim 1, wherein the variable distance is between a distance of far vision and a distance of near or intermediate vision.

5. The optometry device according to claim 1, wherein said at least one optical element is an optical lens.

6. The optometry device according to claim 2, wherein said at least one optical element is movable in rotation and/or in translation between said active position and said retracted position.

7. The optometry device according to claim 1, wherein said screen is movable in translation along a reference axis between two positions corresponding to different distances between the visual test image produced and the exit aperture.

8. The optometry device according to claim 1, wherein said screen is movable in translation along two perpendicular directions for centering said screen relative to an optical axis of said at least one optical element.

9. The optometry device according to claim 7, wherein said at least one optical element is an optical lens in an active position, and
 a relative position of said screen and said optical lens is adjustable for the screen to be located at a distance from said at least one optical element equal to a back focal length of said optical lens measured along an optical axis of said optical lens.

10. The optometry device according to claim 1, wherein said visual test image comprises either the test picture displayed by said screen without influence of said at least one optical element, reflected or not by a reflecting surface of the device or an image of said test picture projected by said at least one optical element, reflected or not by a reflecting surface of the device.

11. The optometry device according to claim 1, wherein relative positions of the screen, said at least one optical element, and the exit aperture are configured to be varied in order for said distance between the visual test image and the exit aperture to be continuously varied in one or several ranges of optical distances between infinity and a near vision distance.

12. The optometry device according to claim 1, further comprising at least one reflecting surface arranged in said device in order to direct the optical path of the light emitted by said screen toward the exit aperture.

13. The optometry device according to claim 12, wherein said at least one reflecting surface is movable in translation and/or in rotation between at least two positions.

14. The optometry device according to claim 13, wherein said at least one reflecting surface is moved in translation and/or in rotation to a position at which said at least one reflecting surface directs the light emitted by said screen toward the exit aperture when said at least one optical element remains out of said optical path.

15. The optometry device according to claim 1, wherein an angular size of the visual test image measured as seen from the exit aperture is between 5° and 25°.

16. The optometry device according to claim 1, further comprising a second screen to display a second picture, an image of the second picture being superimposed with said visual test image at the exit aperture of the device.

17. The optometry according to claim 1, wherein the screen is one of a LCD screen, a TFT screen, an LED or OLED screen, serigraphy with backlight screen, and a display light projection screen with micro video projectors.

18. A method for testing an eye of an individual using an optometry device for testing the eye of the individual, the device comprising a refraction test unit having an optical system for providing different vision correction powers close to the eye of the individual, and a display to produce a visual test image for the eye of the individual, said visual test image being visible through an exit aperture of said test unit of the optometry device, the display comprising:
 a screen to display a test picture used in producing said visual test image, and
 at least one optical element having an optical power,
 said at least one optical element presenting an active state in which the at least one optical element exhibits a non-zero refraction power placed on an optical path of the light emitted by said screen and exiting the device through said exit aperture, and an inactive state in which the at least one optical element introduces no refractive power on said optical path, in order for the visual test image to be produced at a variable distance from said exit aperture the method comprising:
 producing said visual test image for the eye of the individual based on said test picture, said visual test image being visible through said exit aperture of the optometry device through which the eye of the individual may look at said visual test image,
 varying said variable distance between said visual test image and said exit aperture, by changing the state of said at least one optical element between said active state and said inactive state, and
 assessing a visual perception of said visual test image by at least one eye of the individual at different distances between said visual test image and said exit aperture.

19. The optometry device according to claim 4, wherein said at least one optical element is movable in rotation and/or in translation between an active position and a retracted position.

20. The optometry device according to claim 5, wherein said at least one optical element is movable in rotation and/or in translation between an active position and a retracted position.

* * * * *